(12) United States Patent
Emanuel

(10) Patent No.: US 8,061,359 B2
(45) Date of Patent: Nov. 22, 2011

(54) SURGICAL ENDOSCOPIC CUTTING DEVICE AND METHOD FOR ITS USE

(75) Inventor: Mark Hans Emanuel, Bloemendaal (NL)

(73) Assignee: Smith & Nephew, Inc., Memphis, TN (US)

( * ) Notice: Subject to any disclaimer, the term of this patent is extended or adjusted under 35 U.S.C. 154(b) by 750 days.

(21) Appl. No.: 11/780,759

(22) Filed: Jul. 20, 2007

(65) Prior Publication Data

US 2008/0015621 A1   Jan. 17, 2008

Related U.S. Application Data

(63) Continuation of application No. 09/486,977, filed on Mar. 6, 2000, now Pat. No. 7,249,602.

(30) Foreign Application Priority Data

Sep. 4, 1997  (NL) .................................... 1006944

(51) Int. Cl.
*A61F 19/00* (2006.01)
*A61B 17/32* (2006.01)
(52) U.S. Cl. ........................ 128/898; 606/170; 606/15
(58) Field of Classification Search .............. 606/15, 606/170, 185, 22, 180; 604/22, 256; 128/898; 600/104, 127
See application file for complete search history.

(56) References Cited

U.S. PATENT DOCUMENTS

| | | | |
|---|---|---|---|
| 1,666,332 A | 4/1928 | Hirsch | |
| 2,708,437 A | 5/1955 | Hutchins | |
| 3,995,619 A | 12/1976 | Glatzer | |
| 3,996,921 A | 12/1976 | Neuwirth | |
| 4,198,958 A | 4/1980 | Utsugi | |
| 4,203,444 A * | 5/1980 | Bonnell et al. | 604/22 |
| 4,258,721 A | 3/1981 | Parent et al. | |
| 4,261,346 A | 4/1981 | Wettermann | |
| 4,369,768 A | 1/1983 | Vukovic | |
| 4,392,485 A | 7/1983 | Hiltebrandt | |
| 4,414,962 A | 11/1983 | Carson | |
| 4,449,538 A | 5/1984 | Corbitt et al. | |
| 4,543,965 A | 10/1985 | Pack et al. | |
| 4,601,290 A | 7/1986 | Effron et al. | |
| 4,606,330 A | 8/1986 | Bonnet | |
| 4,630,598 A | 12/1986 | Bonnet | |
| 4,706,656 A | 11/1987 | Kuboto | |
| 4,737,142 A | 4/1988 | Heckele | |
| 4,756,309 A | 7/1988 | Sachse et al. | |
| 4,867,157 A | 9/1989 | McGurk et al. | |

(Continued)

FOREIGN PATENT DOCUMENTS

DE    32 06 381    9/1983

(Continued)

OTHER PUBLICATIONS

U.S. Office Action in U.S. Appl. No. 11/929,940, mailed Jul. 1, 2010, 14 pages.

(Continued)

*Primary Examiner* — Vy Q Bui
(74) *Attorney, Agent, or Firm* — Fish & Richardson P.C.

(57) ABSTRACT

A surgical endoscopic cutting device includes cutting elements fitted in a protective tube. The device has an inlet for fluid, a discharge outlet for tissue and fluid, and a further outlet that discharges most of the fluid.

8 Claims, 3 Drawing Sheets

U.S. PATENT DOCUMENTS

| | | | |
|---|---|---|---|
| 4,924,851 A | | 5/1990 | Ognier et al. |
| 4,950,278 A | | 8/1990 | Sachse et al. |
| 4,955,882 A | | 9/1990 | Hakky et al. |
| 4,998,527 A | | 3/1991 | Meyer |
| 4,998,914 A | | 3/1991 | Wiest et al. |
| 5,027,792 A | | 7/1991 | Meyer |
| 5,037,386 A | | 8/1991 | Marcus et al. |
| 5,105,800 A | | 4/1992 | Takahashi et al. |
| 5,106,364 A | | 4/1992 | Hayafuji et al. |
| 5,125,910 A | | 6/1992 | Freitas |
| 5,152,744 A | | 10/1992 | Krause et al. |
| 5,163,433 A | | 11/1992 | Kagawa et al. |
| 5,176,677 A | | 1/1993 | Wuchinich |
| 5,195,541 A | | 3/1993 | Obenchain |
| 5,269,785 A | | 12/1993 | Bonutti |
| 5,312,399 A | | 5/1994 | Hakky et al. |
| 5,320,091 A | * | 6/1994 | Grossi et al. ............ 600/104 |
| 5,347,992 A | | 9/1994 | Pearlman et al. |
| 5,364,395 A | | 11/1994 | West |
| 5,392,765 A | | 2/1995 | Muller |
| 5,409,013 A | | 4/1995 | Clement |
| 5,429,601 A | | 7/1995 | Conley et al. |
| 5,449,356 A | | 9/1995 | Walbrink et al. |
| 5,456,689 A | | 10/1995 | Kresch et al. |
| 5,492,537 A | | 2/1996 | Vancaillie |
| 5,498,258 A | | 3/1996 | Hakky et al. |
| 5,549,541 A | | 8/1996 | Muller |
| 5,556,378 A | | 9/1996 | Storz et al. |
| 5,569,254 A | | 10/1996 | Carlson et al. |
| 5,603,332 A | | 2/1997 | O'Connor |
| 5,630,798 A | | 5/1997 | Beiser et al. |
| 5,730,752 A | | 3/1998 | Alden et al. |
| 5,741,287 A | | 4/1998 | Alden et al. |
| 5,749,885 A | | 5/1998 | Sjostrom et al. |
| 5,759,185 A | * | 6/1998 | Grinberg ............ 606/80 |
| 5,772,634 A | | 6/1998 | Atkinson |
| 5,775,333 A | | 7/1998 | Burbank et al. |
| 5,807,240 A | | 9/1998 | Muller et al. |
| 5,814,009 A | | 9/1998 | Wheatman |
| 5,840,060 A | | 11/1998 | Beiser et al. |
| 5,913,867 A | | 6/1999 | Dion |
| 5,944,668 A | | 8/1999 | Vancaillie et al. |
| 5,947,990 A | | 9/1999 | Smith |
| 5,956,130 A | | 9/1999 | Vancaillie et al. |
| 6,032,673 A | * | 3/2000 | Savage et al. ............ 128/898 |
| 6,039,748 A | | 3/2000 | Savage et al. |
| 6,068,641 A | | 5/2000 | Varsseveld |
| 6,086,542 A | | 7/2000 | Glowa et al. |
| 6,090,123 A | | 7/2000 | Culp et al. |
| 6,113,594 A | | 9/2000 | Savage |
| 6,132,448 A | | 10/2000 | Perez et al. |
| 6,156,049 A | | 12/2000 | Lovato et al. |
| 6,159,160 A | | 12/2000 | Hsei et al. |
| 6,159,209 A | | 12/2000 | Hakky |
| 6,258,111 B1 | | 7/2001 | Ross et al. |
| 6,358,200 B1 | | 3/2002 | Grossi |
| 6,585,708 B1 | | 7/2003 | Maaskamp |
| 6,626,827 B1 | | 9/2003 | Felix et al. |
| 6,632,182 B1 | | 10/2003 | Treat |
| 6,656,132 B1 | | 12/2003 | Ouchi |
| 7,226,459 B2 | | 6/2007 | Cesarini et al. |
| 2002/0058859 A1 | | 5/2002 | Brommersma |
| 2003/0050603 A1 | | 3/2003 | Todd |
| 2005/0043690 A1 | | 2/2005 | Todd |

FOREIGN PATENT DOCUMENTS

| | | |
|---|---|---|
| DE | 36 01 453 | 9/1986 |
| DE | 3615694 A1 | 11/1987 |
| DE | 196 33 124 | 5/1997 |
| EP | 0 327 410 | 8/1989 |
| EP | 0 557 044 | 8/1993 |
| GB | 2 093 353 | 9/1982 |
| JP | 01-75416 | 5/1989 |
| JP | 2002529185 A | 9/2002 |
| WO | 93/07821 | 4/1993 |
| WO | 93/15664 | 8/1993 |
| WO | 95/30377 | 11/1995 |
| WO | 96/11638 | 4/1996 |
| WO | WO0028890 A1 | 5/2000 |

OTHER PUBLICATIONS

U.S. Advisory Action in U.S. Appl. No. 11/929,940, mailed Sep. 10, 2010, 3 pages.

U.S. Office Action in U.S. Appl. No. 11/929,938, mailed Jul. 30, 2010, 15 pages.

U.S. Office Action in U.S. Appl. No. 11/929,940, mailed Dec. 30, 2009, 10 pages.

Japanese Office Action in Application No. 2007-530014, dated Feb. 15, 2011, 10 pages.

U.S. Office Action in U.S. Appl. No. 11/929,938, mailed Jan. 5, 2011, 10 pages.

* cited by examiner

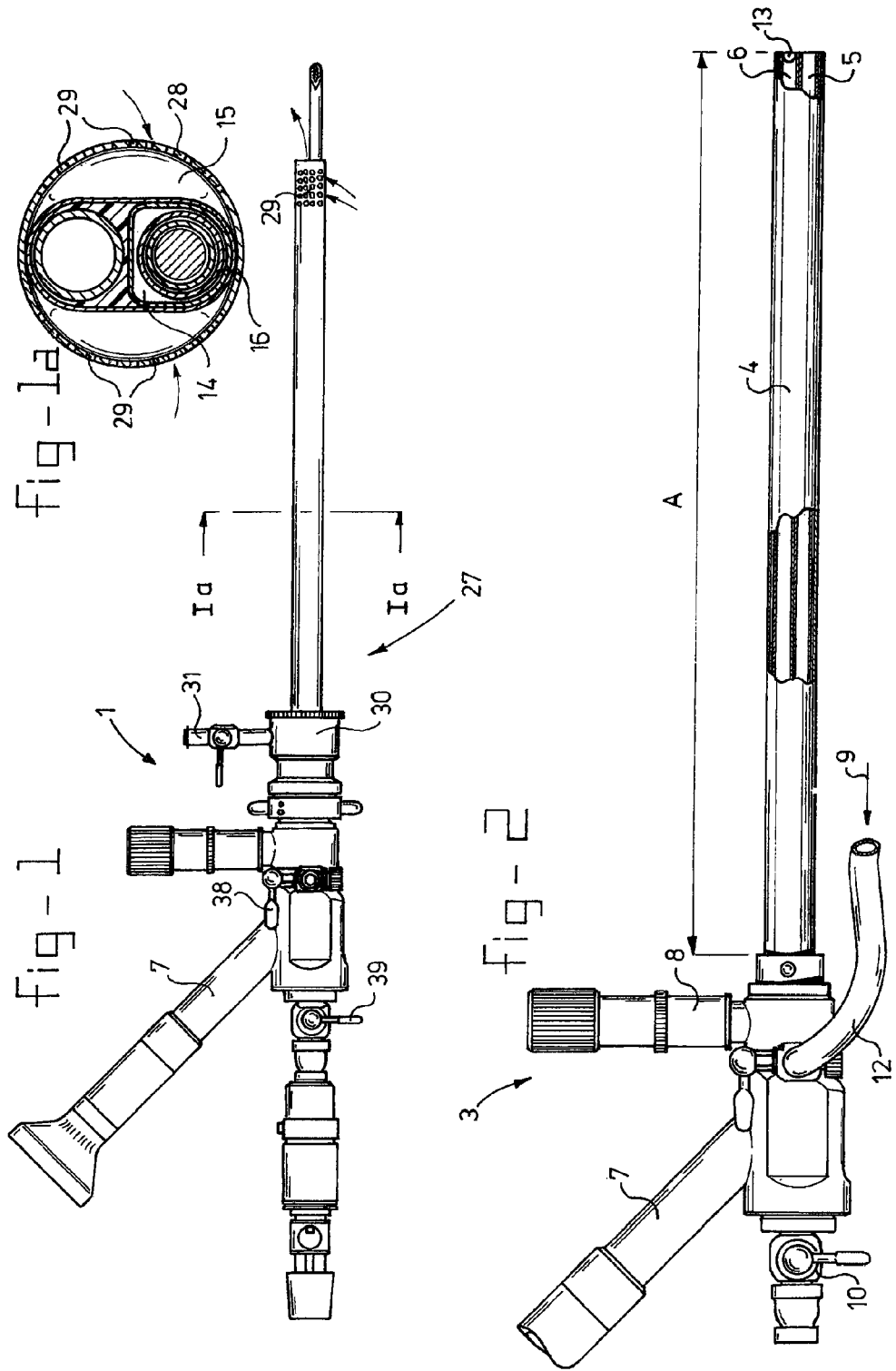

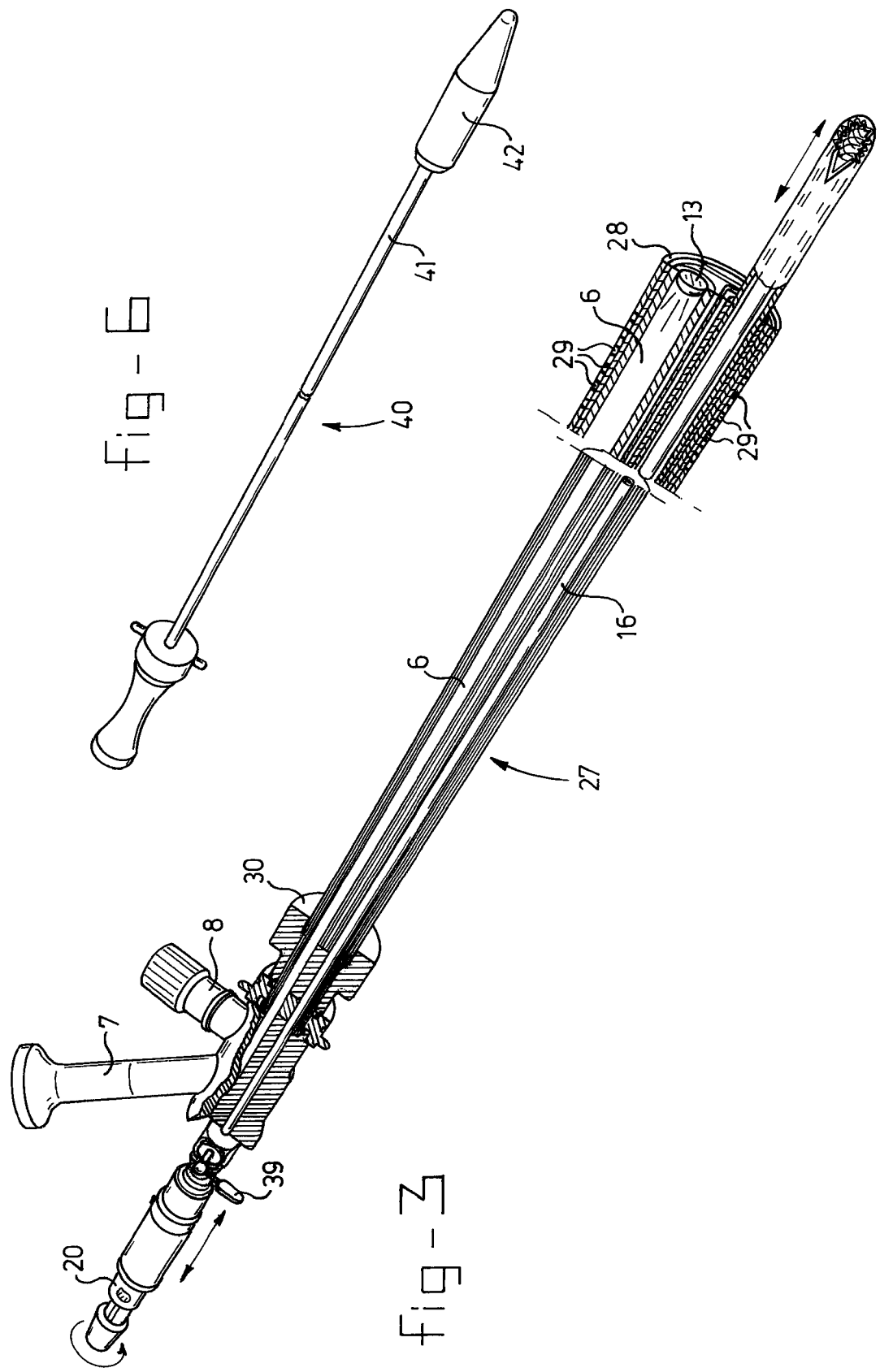

SURGICAL ENDOSCOPIC CUTTING DEVICE AND METHOD FOR ITS USE

CROSS-REFERENCE TO RELATED APPLICATIONS

This application is a continuation application of and claims priority to U.S. application Ser. No. 09/486,977, filed on Mar. 6, 2000.

FIELD OF THE INVENTION

The present invention relates to a surgical endoscopic cutting device.

BACKGROUND OF THE INVENTION

Surgical cutting devices are generally known and used for the removal of hard and/or soft tissue, such as in the vicinity of the knee joint. Such cutting devices are used in, for example, a joint cavity, where they can be guided endoscopically by separately inserting a viewing device having a light source and an observation portion. Such operations are successfully used in organs and joints lying not too deep underneath the skin.

When operations are being carried out on organs lying deeper, other techniques are currently used. If, for example, tissue has to be removed from the uterus, prostate, or urinary bladder, such as mucous membrane or other tissues, it was customary until now to use a so-called "loop." This is a loop-shaped cutting wire which is brought to a first potential, while the wall of the uterus is brought to a second, different potential. Tissue is removed by moving the loop along the uterus wall. In order to be able to carry out such an operation, it is necessary to dilate the uterus. Dilation is carried out by introducing a fluid. In order to maintain the effect of the potential difference, a non-conducting fluid is used, for example a 5% sorbitol solution. Because wounds are caused during the treatment described above, a good part of this fluid is resorbed into the patient's bloodstream (by way of the uterus). This can lead to highly dangerous electrolyte displacements. It has been found that the tissue can be removed more easily by working with a high-frequency monopolar electric current, but there is a risk of high-frequency electric current leading to internal and external burns. The loop is generally fitted on an endoscope and moved back and forth along the uterus wall with the endoscope. The tissue cut off during this treatment has to be removed from the uterus, which considerably extends the duration of the operation. Furthermore, the doctor has to check that all detached material actually has been removed.

This means that such operations are very time-consuming and require the surgeon to repeatedly move the device back and forth. This is tiring and consequently difficult to learn. Moreover, the patient has to be monitored continually during the operation, in order to prevent the undesirable phenomena described above. It is not uncommon for such an operation to be broken off because the patient's life is endangered by the side effects.

On the other hand, it is desirable to be able to carry out such operations instead of simply performing a hysterectomy.

WO 96/11638 discloses a cutter including a hollow stem and a cutting head accommodated inside a rigid housing. This rigid housing likewise contains a viewing channel with the necessary optics. U.S. Pat. No. 5,195,541 describes a laparoscopic discectomy apparatus. For a laparoscopic method it is essential to inflate the related cavity using gas. The gas feed is discontinuous and has no effect on viewing of the operation site.

Fluid is introduced by way of a space between the stem and the rigid housing and discharged together with the detached tissue through the hollow stem of the cutter.

This device could be satisfactory for the removal of tissues from certain body cavities, such as from the bladder. However, in the case of other body cavities, it is necessary to "blow up" the cavity before treatment can be carried out. An example of this is the uterus, in which it is important that the amount of enlargement of the organ be accurately controlled. The irregular discharge of fluid through the hollow stem of the cutter, caused partly by the irregular release of tissue, means that it cannot be guaranteed that the pressure inside the cavity is accurately controlled.

Such a device is consequently not very suitable for use in the treatment of such a cavity.

SUMMARY OF THE INVENTION

The object of the present invention is to provide a device which can perform such a treatment.

According to the invention, a further outlet channel is provided, the function of which is independent of whether or not detached tissue has been released. In other words, a regular discharge of fluid can occur through this further outlet channel. Since only a minor part of the fluid is now discharged through the outlet, in which there are detached pieces of tissue, the pressure inside the body cavity can be regulated and controlled accurately. This makes it possible to remove undesired tissue from cavities such as the uterus. The applicability of the removal of tissues by cutting is consequently considerably increased.

The further outlet channel described above is formed by an insertion tube fitted around the endoscopic device. This insertion tube serves to clear a space for the endoscopic device. For this purpose, the front side of the insertion tube can be provided with an insertion mandrel, which is removed after the positioning of the insertion tube and replaced by the endoscopic device described above. In this case the further outlet channel can be defined between the endoscopic device and the insertion tube.

In the case of such a construction it is desirable for a coupler to be present to provide a coupling between the rigid housing and the insertion tube described above.

Discharge of the tissue material which has been detached can be achieved either by making the stem on which the cutting elements are fitted hollow, or by fitting a protective tube around the cutter. Such a protective tube can also be used without the space between protective tube and stem serving as an outlet channel. This means that the cutter can be designed as a separate unit which can be coupled to the rigid housing, which has advantages in particular for purposes of sterilization. Namely, the device can then be detached in a simple way.

For the removal of tissue from a uterus it is essential for the rigid housing to have a length which is sufficient to reach all tissue parts, i.e. a length of at least 30 cm.

The observation part of the device described above includes a light channel in the housing, provided near one end with a lens and near the other end with an observation mechanism. The latter can include an eyepiece or a connection for a camera so that the surgeon can carry out the operation using a monitor and others can possibly look at the same time.

The cutting elements described above can include any cutting element known in the prior art. In other words, a cutting head with cutting faces can be used, but it is also possible to use constructions with teeth, meshing with the protective tube or otherwise. In the latter instance, the protective tube is preferably provided with a lateral opening through which a part of the cutting elements extends so that on each revolution, part of the tissue is removed and can be discharged directly through the interior of the drive/discharge tube of the cutter.

The invention also relates to a method for the removal of uterus tissue in which the device described above is used. In other words, a machining operation is now applied with the use of a physiological fluid which can be electrically conducting without any problem, while at the same time the removed tissue is sucked out. It is, of course, possible to suck out the tissue at a later stage. The machining operation is carried out by a rotating action.

According to a further embodiment of the method, an outlet and a further outlet are present, and the pressure inside the body cavity is regulated by metering the quantity of fluid which moves through the further outlet. The insertion of the surgical endoscopic cutting device is preferably carried out in the manner described above using an insertion mandrel and insertion tube.

BRIEF DESCRIPTION OF DRAWINGS

The invention will be explained in greater detail below with reference to an exemplary embodiment shown in the drawings, in which:

FIG. 1 shows the endoscopic cutting device according to the invention in the assembled state, in side view and partially in section;

FIG. 1a shows the viewing/receiving part of the cutting device of FIG. 1 in section along the line Ia-Ia;

FIG. 2 shows a side and partially cut-away view of the viewing/receiving part of the cutting device of FIG. 1;

FIG. 3 shows a partially cut-away perspective view of the device of FIG. 1, with the insertion end enlarged;

FIG. 6 shows an insertion mandrel according to the invention.

DETAILED DESCRIPTION

Figures 4, 5:
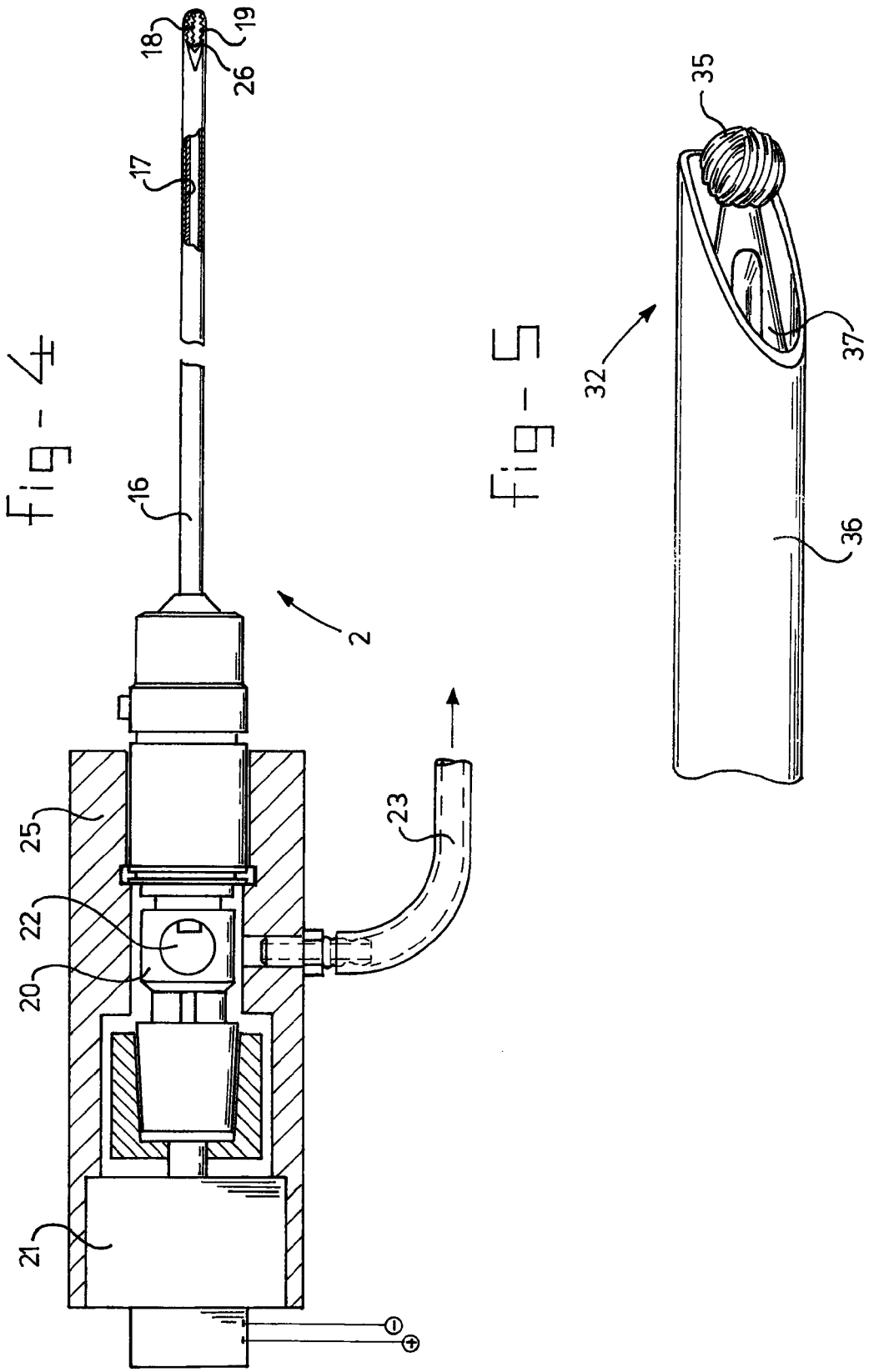
FIG. 4 shows a partially sectional side view of the cutter of the cutting device of FIG. 3.
FIG. 5 shows a variant of the cutter shown in FIG. 4.

The endoscopic cutting device according to the invention is indicated in its entirety by 1 in FIG. 1. It comprises a viewing/receiving part 3, which is shown in FIG. 2, a cutting part 2, which is shown in greater detail in FIGS. 4 and 5, and an insertion mandrel, which is shown in FIG. 6.

With reference to FIG. 2, it can be seen that the viewing/receiving part 3, is composed of an outer tube 4 in which a main channel 5 and viewing channel 6 are defined. Viewing channel 6 ends at one side in a lens 13 and at the other side in a viewing tube 7, on which an eyepiece or camera connection is placed. A connection 8 for a light source is also present, for connection to a light guide, such as a fibre optics bundle, which provides for lighting at the end of lens 13. Near the control end, tube 4 is provided with a fluid inlet 9 connected to a hose 12, for adding a physiological salt solution.

A shut-off valve is indicated by 10.

The length of the actual outer tube 4, is indicated by A and is more than 30 cm.

FIG. 4 shows details of the cutter or the cutting part 2, which is composed of a protective tube 16 inside of which a drive/suction tube 17 is fitted. Near the working end, tube 17 is provided with teeth 19 which mesh with teeth 18 provided in an opening 26 in the end part of protective tube 16. Near the other end, drive/suction tube 17 is provided with a coupling 20, which can be connected at one end to a rotating drive motor 21, not shown in detail, and at the other end is provided with an opening 22 through which fluid and removed material can be discharged by way of suction tube 17 to the discharge hose 23. A pressure regulator can be present in this discharge hose 23, which is connected to a vacuum source.

In FIG. 1 the insertion part is indicated by 27. This insertion part is composed of an insertion tube 28 which is provided with openings 29 at one end and near the other end, the insertion part 27 is provided with a bayonet connection 30 and an outlet 31. Insertion tube 28 is designed in such a way that tube 4 can be fitted therein, as shown in FIGS. 1 and 3, while it is also possible to fit insertion mandrel 40, provided with stem 41 and mandrel 42, in insertion tube 28

The construction described above has an inlet 38 for fluid. Inlet 38 extends to channel 14 (FIG. 1a), i.e. the space bounded between the outer tube 4 and the protective tube 16 and 36, respectively from FIGS. 4 or 5. A shut-off valve 39, which is connected to channel 14, is present, while the further outlet is indicated by 31. A discharge hose 23 for tissue and fluid is shown. During the removal of tissue, with a substantially continuous supply of fluid through inlet 38, some of the fluid will be discharged through outlet 23. This relatively small amount will be mixed with a mixture released during the cutting operation. Most of the fluid will be discharged through the further outlet 31. This discharge is unimpeded and occurs through openings 29. Pressure variations occurring due to the presence or absence of removed tissue in channel 17 (FIG. 4) have little or no influence on the pressure inside the body cavity owing to the presence of the further outlet 31.

If the device is to be inserted into, for example, a uterus, insertion mandrel 40 will first be inserted, with shut-off valve 39 open, into insertion tube 28 with bayonet 30. This assembly is then placed in the uterus in a relatively simple manner due to the shape of mandrel 42. Mandrel 42 is then removed by manipulating stem 41, and the construction shown in FIG. 2 is placed in tube 28. Connection is made here to bayonet 30. The cutting action can then begin after the uterus has been dilated by the introduction of fluid. This fluid can be a physiological flushing and distension fluid, such as a physiological salt solution (NaCl 0.9%). In the event of the (unavoidable) resorption of the physiological fluid into the blood, electrolyte displacement, with fatal consequences for the patient, will not occur. Owing to the absence of electrical current, the burns described above are also ruled out.

By switching on motor 21, tube 17 is set in rotation and teeth 19 move regularly along cutting edge 18 of protective tube 16 which remains stationary. While they are moving along each other and picking up tissue material between them, a cutting, detaching action on the tissue material is occurring. The cut, detached material is removed through the interior of tube 17 and outlet 23.

The appropriate area of the uterus can be treated by moving parts 18 and 19 along the uterus wall or along tissue to be removed, which can be observed through viewing tube 7 by supplying light through connection 8.

Through the use of a continuous flow system, a constantly clear view is obtained for the observer even if blood and/or mucous is/are in the mixture. Moreover, the pressure can be maintained as low as possible, in order to prevent intravasation.

FIG. 5 shows a variant of the end of the cutter. The cutter or cutting part are indicated in their entirety by 32. The protective tube is indicated by 36 and is beveled near the end. The drive/suction tube is indicated by 37 and provided with a cutting head near the end. In this embodiment, there is either no interaction between cutting head 35 and protective tube 36, or head 35 and tube 36 interact near the edge of tube 36, which is adapted for that purpose by grinding.

It is understood that such cutting elements can be designed in any way known in the prior art.

These and further modifications are considered to lie within the scope of the present application, to be immediately obvious to the person skilled in the art after reading the description, and to lie within the scope of the appended claims. For instance, it is possible to effect the supply of working fluid and the discharge of cleaning material in another way, i.e., to arrange the interior of housing 4 slightly differently. Furthermore, the method described above can be used for the removal of other tissue material, such as prostate tissue through the urethra, or for the removal of tissue from the wall of the urinary bladder.

What is claimed is:

1. A method for removal of tissue from a uterus, comprising:
    inserting a distal region of an endoscope into said uterus, the endoscope including a valve and an elongated member defining discrete first and second channels extending from a proximal region of the elongated member to the distal region, the second channel having a proximal end in communication with the valve such that fluid from the valve is able to flow into and through the second channel to the uterus, and the first channel having a light guide permanently affixed therein and being sealed from the second channel to prevent fluid from the valve from entering the uterus through the first channel; followed by:
    inserting a motor driven cutter into the second channel such that a distal cutting region of the cutter extends distally beyond the endoscope in the uterus;
    delivering fluid into the uterus through the valve and the second channel to distend the uterus;
    energizing an electric motor to drive the cutter to cut tissue within the uterus; and
    aspirating cut tissue and fluid from the uterus and the endoscope through the cutter.

2. The method of claim 1 wherein inserting the motor driven cutter comprises inserting an outer tube defining a cutting window at a distal region of the outer tube and an inner tube received within the outer tube that is configured to rotate relative to the outer tube to cut tissue, the inner tube including a cutting element at a distal region of the inner tube configured to cut tissue at the cutting window when the inner tube rotates relative to the outer tube.

3. The method of claim 1, wherein inserting the distal region of the endoscope comprises inserting a distal region of an endoscope that includes a fiber optics bundle permanently affixed to the first channel of the elongated member.

4. The method of claim 1, wherein inserting the distal region of the endoscope comprises inserting a distal region of an endoscope that includes a lens permanently affixed to the first channel of the elongated member.

5. A method for removal of tissue from a uterus, comprising:
    inserting a distal region of an endoscope into the uterus, the endoscope including a port for receiving a motor driven cutter and including an elongated member defining discrete first and second channels extending from a proximal region of the elongated member to the distal region, the first channel having a light guide permanently affixed therein and the second channel having a straight, central longitudinal axis extending from the port to an opening at a distal tip of the endoscope; followed by:
    inserting the motor driven cutter for cutting and detaching tissue into the second channel through the port;
    introducing fluid into the uterus; and
    aspirating fluid with detached tissue from the uterus through a lumen of the cutter.

6. The method of claim 5 wherein inserting the motor driven cutter comprises inserting an outer tube defining a cutting window at a distal region of the outer tube and an inner tube received within the outer tube that is configured to rotate relative to the outer tube to cut tissue, the inner tube including a cutting element at a distal region of the inner tube configured to cut tissue at the cutting window when the inner tube rotates relative to the outer tube.

7. The method of claim 5, wherein inserting the distal region of the endoscope comprises inserting a distal region of an endoscope that includes a fiber optics bundle permanently affixed to the first channel of the elongated member.

8. The method of claim 5, wherein inserting the distal region of the endoscope comprises inserting a distal region of an endoscope that includes a lens permanently affixed to the first channel of the elongated member.

* * * * *